US011515044B1

(12) United States Patent
Roh et al.

(10) Patent No.: US 11,515,044 B1
(45) Date of Patent: Nov. 29, 2022

(54) SYSTEM FOR ADMINISTERING A QUALITATIVE ASSESSMENT USING AN AUTOMATED VERBAL INTERFACE

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX INNOVATION LLC, Seattle, WA (US)

( * ) Notice: Subject to any disclaimer, the term of this patent is extended or adjusted under 35 U.S.C. 154(b) by 0 days.

(21) Appl. No.: 17/567,092

(22) Filed: Dec. 31, 2021

(51) Int. Cl.

| | |
|---|---|
| ***G06K 9/00*** | (2022.01) |
| ***G16H 50/30*** | (2018.01) |
| ***G10L 13/02*** | (2013.01) |
| ***G10L 15/22*** | (2006.01) |
| ***G10L 15/18*** | (2013.01) |
| ***G06T 7/20*** | (2017.01) |
| ***G06V 40/20*** | (2022.01) |
| ***G10L 25/66*** | (2013.01) |
| ***G16H 10/60*** | (2018.01) |
| ***G16H 50/20*** | (2018.01) |
| ***G06T 7/00*** | (2017.01) |

(52) U.S. Cl.

CPC .......... *G16H 50/30* (2018.01); *G06T 7/0012* (2013.01); *G06T 7/20* (2013.01); *G06V 40/20* (2022.01); *G10L 13/02* (2013.01); *G10L 15/18* (2013.01); *G10L 15/22* (2013.01); *G10L 25/66* (2013.01); *G16H 10/60* (2018.01); *G16H 50/20* (2018.01); *G06T 2207/20081* (2013.01); *G06T 2207/30004* (2013.01); *G06T 2207/30196* (2013.01)

(58) Field of Classification Search

CPC ........ G16H 50/30; G16H 10/60; G16H 50/20; G06T 7/0012; G06T 7/20; G06T 2207/20081; G06T 2207/30004; G06T 2207/30196; G06V 40/20; G10L 13/02; G10L 15/18; G10L 15/22; G10L 25/66

See application file for complete search history.

(56) References Cited

U.S. PATENT DOCUMENTS

2016/0378747 A1* 12/2016 Orr ........................ G06F 40/279 704/9
2017/0354846 A1* 12/2017 Von Rueckmann ..... G09B 5/00
2021/0217508 A1* 7/2021 Kosofsky ............... G01K 13/00

* cited by examiner

*Primary Examiner* — Tom Y Lu

(74) *Attorney, Agent, or Firm* — FisherBroyles, LLP; Jeremy P. Sanders

(57) ABSTRACT

Using artificial intelligence and data observed using sensors or imaging devices to prompt a patient to provide responses or perform actions and then observing the patient's responses to the prompts and performing an assessment resulting in a quantitative result. The quantitative result is then used to complete a clinical qualitative assessment of the patient.

20 Claims, 7 Drawing Sheets

| Record ID | Visit ID | Patient ID | Date | Time | Gender | Age | Weight | Height | Pulse | SpO2 | Blood Pressure | Pre-existing Conditions | Allergies | Medications |
|---|---|---|---|---|---|---|---|---|---|---|---|---|---|---|
| 368547 | 635468 | 32104 | 6/21/2021 | 2:08:06 PM | Male | 21 | 170 | 70 | 110 | 94 | 140/95 | None | None | Albuterol |
| 368548 | 635467 | 35468 | 6/21/2021 | 2:16:42 PM | Male | 45 | 230 | 72 | 100 | 97 | 125/85 | Diabetes | penicillin | None |
| 368549 | 635466 | 32189 | 6/21/2021 | 2:18:30 PM | Female | 16 | 180 | 62 | 120 | 96 | 130/90 | None | None | None |
| 368550 | 635465 | 12368 | 6/21/2021 | 2:18:52 PM | Female | 31 | 150 | 60 | 85 | 98 | 130/95 | None | Latex | None |
| 368551 | 635464 | 26874 | 6/21/2021 | 2:22:45 PM | Male | 52 | 210 | 68 | 160 | 84 | 180/110 | Hypertension | None | Aspirin |
| 368552 | 635463 | 33546 | 6/21/2021 | 2:30:00 PM | Female | 72 | 165 | 65 | 95 | 99 | 150/100 | None | None | None |
| 368553 | 635462 | 36984 | 6/21/2021 | 2:48:35 PM | Female | 65 | 200 | 68 | 110 | 100 | 160/105 | Diabetes | None | None |

Patient Database

FIG. 2

| Assessment | Assessment Type | Score Range | Clinical Result |
|---|---|---|---|
| Berg Balance Scale | Fall Risk | >55 | Functional Balance |
| Berg Balance Scale | Fall Risk | 45-55 | Minimal Fall Risk |
| Berg Balance Scale | Fall Risk | <45 | Increased Fall Risk |
| Glasgow Coma Scale | Coma Severity | 15 | Best Response |
| Glasgow Coma Scale | Coma Severity | 9 -14 | Responsive |
| Glasgow Coma Scale | Coma Severity | 4-8 | Comatose |
| Glasgow Coma Scale | Coma Severity | 3 | Unresponsive |

Qualitative Assessment Datebase

FIG. 3

Qualitative Assessment Module

Training Module

Monitoring Module

SYSTEM FOR ADMINISTERING A QUALITATIVE ASSESSMENT USING AN AUTOMATED VERBAL INTERFACE

BACKGROUND

The present disclosure is generally related to assessing a patient, particularly obtaining subjective patient data.

Much of modern medicine is still limited by the ability of a medical professional to quantify a patient's symptoms based on subjective observations or complaints of subjective symptoms by a patient. Examples of subjective observations include the severity of pain, level of alertness or consciousness, fall risk, etc. However, the reliability of these scales can vary based on the observer or patient, and most require a medical professional to be present to provide prompts for patient feedback or make direct observations of the patient.

Telemedicine is often limited by the interface through which professionals communicate with their patients. Unfortunately, some assessments must be performed in person, despite not otherwise requiring the presence of a medical professional. This is because most communication interfaces lack adequate motion tracking or depth perception to facilitate a subjective assessment of a patient.

While telemedicine can improve patients' access to diagnostic care, it does not help address the limited availability of medical professionals to perform diagnostic assessments. This creates a bottleneck at the entry of care and requires that a care provider assess each patient before being assigned a priority. This process consumes significant resources without rendering care while taking resources away from those with a critical need. Further, it limits the number of people who can be served by a group of medical professionals in a given period. What is needed is a way to reduce the burden on care providers while collecting critical diagnostic data.

Some qualitative assessments, such as quantifying pain, assessing the likelihood of a stroke in a prehospital setting, or measuring a patient's range of movement, gait, or other physiological function where an objective test is not available, require a trained professional to administer an exam. Using an automated system to provide consistent and clear instructions to the patient and sensors to measure the patient's response, the measurements may be standardized and become objectively more consistent and comparatively useful. A trained professional is no longer required, and the results are consistent as there is limited variability in the instructions given and how the patient's responses, whether verbal or physical, are measured and classified. This allows these qualitative assessments to become similar in value to objective measurements and tests. These and other features will become readily apparent by the following description of some preferred embodiments.

SUMMARY

According to some embodiments, a method is under control of one or more computing devices, and includes the steps of receiving, from a patient database, patient data associated with a patient; receiving, from a qualitative assessment database, a score associated with a previous qualitative assessment; selecting a qualitative assessment to be performed; prompting, based at least in part on the qualitative assessment, the patient to perform a physical action; generating, from one or more sensors, motion data associated with the physical action of the patient; and determining, based at least in part on the motion data, a qualitative assessment, the qualitative assessment including a qualitative assessment score.

In some embodiments, the qualitative assessment module comprises a machine learning model and further comprising training the machine learning model on medical training data and medical ground truth data.

The method may include the step of generating, by the one or more computing devices, an audible question to the patient and receiving an audible answer from the patient.

In some examples, generating an audible question comprises a text to speech converter that generates the audible question. The method may include performing natural language processing on the audible answer and determining, based at least in part on the audible answer, the qualitative assessment.

In some cases, generating motion data is performed by one or more wearable sensors on the patient. The one or more wearable sensors may include one or more of a watch, a smart phone, a glove, glasses, a finger monitor, an implantable device, a device in contact with the skin of a patient, or a hat.

In some cases, generating the motion data is performed by one or more of a wearable sensor worn by the patient or an imaging sensor aimed at the patient.

The method may include the step of determining the physical action of the patient by comparing the motion data against a kinematic model.

In some embodiments, the method includes comparing the motion data associated with the patient with historical motion data from the patient database and determining that the motion data associated with the patient is within a normal range for the patient.

The method may include the step of determining, based at least in part on the qualitative assessment score, a diagnosis for the patient, the diagnosis indicating a medical condition and a probability that the medical condition is present.

In some examples, the method includes determining that an additional qualitative assessment is needed and performing an additional qualitative assessment of the patient.

According to some embodiments, a system for assessing a medical patient, comprises a sensor configured to obtain sensor data associated with physical information about a patient; a processor configured to process the sensor data to determine a quantitative assessment score; and an assessment engine configured to determine a qualitative assessment based at least in part on the quantitative assessment score.

The system may include a machine learning model trained on patient data and configured to determine the qualitative assessment. In some examples, the sensor comprises a microphone and further comprising a natural language processing engine configured to convert an audible patient response to text.

According to some embodiments, the sensor comprises a motion sensor affixed to the patient and is configured to obtain motion data of the patient.

The sensor may be an imaging sensor configured to obtain imaging data of the patient and further comprising an image analysis engine configured to analyze the imaging data to determine whether the imaging data is within a normal range for the patient.

The assessment engine may be configured to determine the qualitative assessment based at least in part on one or more of motion data, audible responses, and imaging data of the patient.

In some examples, the assessment engine is configured to determine whether a second quantitative assessment score is needed and obtain second sensor data to determine the second quantitative assessment score.

In some instances, the assessment engine is configured to determine a confidence score for the qualitative assessment.

BRIEF DESCRIPTION OF THE DRAWINGS

The accompanying drawings are part of the disclosure and are incorporated into the present specification. The drawings illustrate examples of embodiments of the disclosure and, in conjunction with the description and claims, serve to explain, at least in part, various principles, features, or aspects of the disclosure. Certain embodiments of the disclosure are described more fully below with reference to the accompanying drawings. However, various aspects of the disclosure may be implemented in many different forms and should not be construed as being limited to the implementations set forth herein. Like numbers refer to like, but not necessarily the same or identical, elements throughout.

FIG. 2 illustrates a patient database, in accordance with some embodiments;

FIG. 3 illustrates a qualitative assessment database, in accordance with some embodiments;

DETAILED DESCRIPTION

Figure 1:
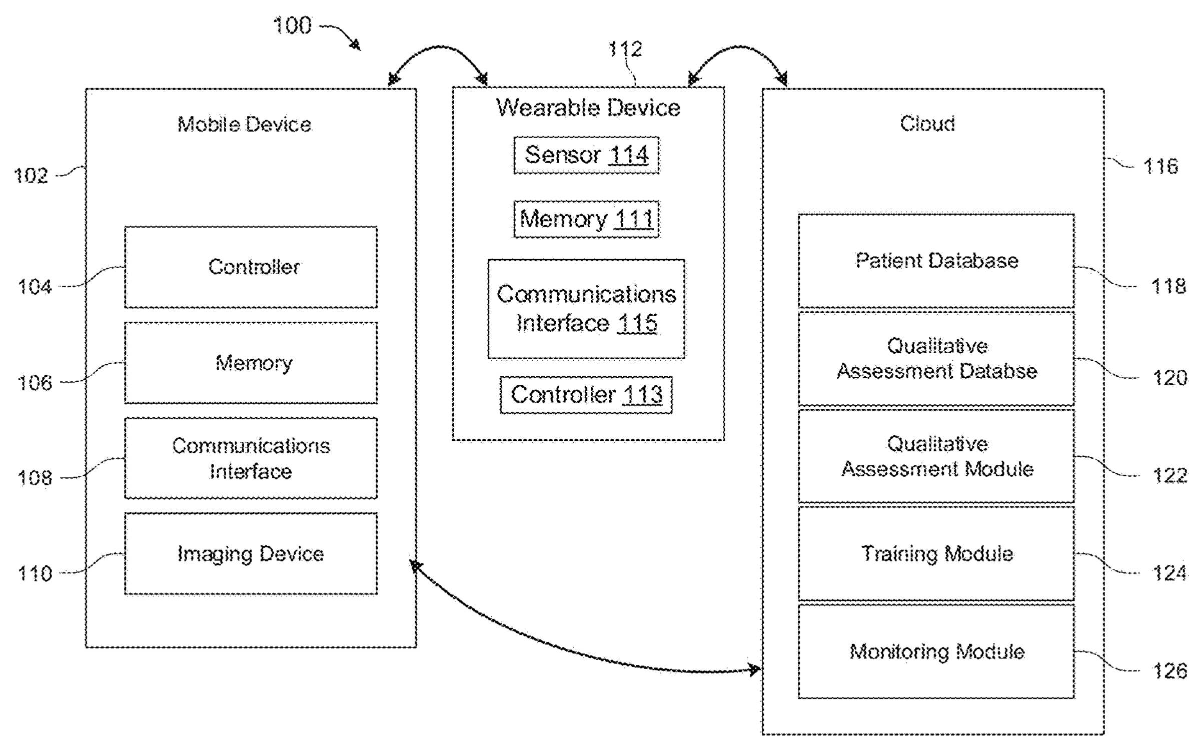
FIG. 1 illustrates a system for an assessment virtual assistant, in accordance with some embodiments.

Advanced surgical systems include many different types of equipment to monitor and anesthetize the patient, assist the surgeon in performing surgical tasks, and maintain the environment of the operating room. Non-limiting examples of surgical equipment that may be used or improved by the present invention are provided for reference.

Vital signs monitor refers to medical diagnostic instruments and in particular, in some cases, to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into some embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into some embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into some embodiments in a variety of manners.

End Tidal CO2 monitor or a capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation, and analgesia, pulmonary diseases such as obstructive pulmonary disease, pulmonary embolism, etc., heart failure, metabolic disorders, etc. The instrument can be configured as side stream (diverting) or mainstream (non-diverting). Diverting device transports a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into some embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into some embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into some embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into some embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, and cardiomyopathy, among others. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into some embodiments in a variety of manners.

Neuromonitoring, also called Intraoperative neurophysiological monitoring (abbreviated as IONM), refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into some embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into some embodiments in a variety of manners.

Somatosensory evoked potential abbreviated as SSEP, or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into some embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into some embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into some embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, ultrasound, X-rays, computed tomography, magnetic resonance imaging, nuclear medicine imaging, positron emission tomography, arthrogram, myelogram, mammography, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into some embodiments in a variety of manners.

A microscope refers to an instrument that is used for viewing samples and objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), Transmission Electron Microscope abbreviated as TEM (electron illuminated and image seen with the microscope is the high magnification and high resolution). A microscope can be integrated into some embodiments in a variety of manners.

Endoscopes or arthroscopes or laparoscopes refer to minimally invasive surgical techniques where procedures are performed by performing minimal incision in the body. An Endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into some embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiber-optic sensors may be intrinsic or extrinsic. Fiber optics sensors may be categorized into four types physical, imaging, chemical, and biological. Fiber optics can be integrated into some embodiments in a variety of manners.

Ultrasound refers to using sound waves to produce images of the inside of a body. In many cases, an ultrasound may be used by placing a small probe on the skin of a patient. In some cases, an ultrasound may be inserted into natural body openings, such as the anus in the case of a transrectal ultrasound probe (TRUS). The ultrasound emits high-frequency sound waves into the body. In some cases, a gel is placed on the skin to facilitate sound transmission and movement of the ultrasound. A computing device may be connected to the probe and receives sound waves that are reflected off of body tissues and creates an image. Ultrasound can be integrated into some embodiments in a variety of manners.

X-ray refers to radiography using x-ray radiation to produce a picture of the targeted body part below the skin. It may often be used to visualize and diagnose bone ailments, infections, injury, or locating foreign objects. X-ray may be integrated into some embodiments in a variety of manners.

Computed tomography (CT scan) refers to a combination of X-ray images taken from multiple angles. The plurality of X-ray images may be combined by a computing device to generate cross-sectional images of the bones, blood vessels, and soft tissues. A CT scan may be used for diagnostic purposes. CT scan may be integrated into some embodiments in a variety of manners.

Magnetic resonance imaging (MRI) refers to applying a magnetic field, such as through radio waves, and a computing device to receive the reflected magnetic field to produce images of organs and tissues. MRI may be integrated into some embodiments in a variety of manners.

Nuclear medicine imaging refers to producing images by detecting radiation from different parts of the body after a radioactive tracer material is administered, which may be intravenously, orally, or otherwise. Nuclear medicine imaging may be integrated into some embodiments in a variety of manners.

Positron emission tomography refers to an imaging technique that uses radioactive substances such as radiotracers to visualize and measure changes in metabolic processes and in other physiological activities including blood flow, regional chemical composition, and absorption, among others. Positron emission tomography may be integrated into some embodiments in a variety of manners.

Arthrogram refers to a diagnostic imaging procedure that uses X-rays to guide and evaluate the injection and/or flow paths of contrast medial directly into a joint. It may used as procedure to supplement imaging data obtained through an MRI or CT scan. Arthrogram may be integrated into some embodiments in a variety of manners.

Myelogram refers to injecting a special dye and X-ray imaging to capture images of the special dye. It can be used to obtain imaging data of the bones and fluid-filled spaces between the bones. In many cases, a myelogram is performed in conjunction with a CT scan to take advantage of the dye injected into the body. A myelogram may be integrated into some embodiments in a variety of manners.

Mammography refers to using low energy X-rays to examine breast tissue, such as for early detection of breast cancer. It may be used for diagnostic purposes and may be used to render 3D images to detect tumors. Mammography may be integrated into some embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into some embodiments in a variety of manners.

High-definition monitors refer to a display in which a clearer picture than possible with low-definition, low-resolution screens. High-definition monitors have a higher density of pixels per inch than past standard TV screens. Resolution for high-definition monitors may be 1280×720 pixels or more. Full HD—1920×1080, Quad HD—2560×1440, 4K—3840×2160, 8K—7680×4320 pixels. High-definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High-definition monitors can be integrated into some embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into some embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, joint, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, liquid jet, sensors, etc. A surgical tower can be integrated into some embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into some embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into some embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into some embodiments in a variety of manners.

Liquid jet involves using a high-pressure fluid stream, such as water, aimed at tissue. The liquid pressure may impinge on the targeted tissue and may be used to cut, incise, perforate, and/or ablate the target tissue. In some cases, the liquid jet creates cavitations that may be used to ablate a volume of tissue. Liquid jet may be integrated into some embodiments in a variety of manners.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into some embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and nuclear medicine e.g., Positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into some embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into some embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MRI instruments may consist of magnets, gradients, radiofrequency systems, computer control systems. Some areas where imaging by MRI should be prohibited may be people with implants. MRI can be integrated into some embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into some embodiments in a variety of manners.

Stereotactic navigation systems refer to an instrument that uses patient imaging (e.g., CT, MRI) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into some embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into some embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machines may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into some embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into some embodiments in a variety of manners.

Disposable air warmer (also referred to as Bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into some embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into some embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into some embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controllers can be integrated into some embodiments in a variety of manners.

Operating room environmental controls refers to control or maintenance of the environment in an operation theatre where procedures are performed to minimize the risk of airborne infection and provide a conducive environment for everyone in the operation theatre-surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into some embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into some embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into some embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into some embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into some embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. A scalpel can be integrated into some embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into some embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Staples may be made of surgical grade stainless steel or titanium, and they are thicker, stronger, and larger. The stapler can be integrated into some embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into some embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into some embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into some embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into some embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, Hospital & Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into some embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into some embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radio-frequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into some embodiments in a variety of manners.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure. Quantum computing can be used with one or more embodiments in a variety of manners.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

FIG. 1 is a system for an assessment virtual assistant 100. This system comprises a mobile device 102, which in some embodiments, is a computing device characterized by being portable. A mobile device 102 may include any one or more of a mobile phone, tablet, laptop, wearable device such as a smart watch, smart glasses, or other type of wearable sensor devices, a portable gaming device, or a proprietary device built for a specific purpose.

In some cases, a mobile device 102 includes a controller 104, memory 106 and a communications interface 108. In some embodiments, a mobile device 102 may be functionally replaced by a stationary computing device such as a desktop computer or server. A mobile device 102 may additionally include or communicate with a quantum computing device.

A controller 104 is a logic device or processor for performing a series of logic operations. Traditionally, a controller 104 is comprised of transistors arranged on a silicon substrate, although a controller 104 may be comprised of any materials and substrates which form a logic circuit. Common logic circuit elements include OR gates, AND gates, XOR gates, NOR gates, NAND gates, etc. A controller 104 may be a microcontroller, a central processing unit (CPU), or microprocessor, that may be part of a computer or computing device. Similarly, a graphical processing unit (GPU) may be used as a controller. A controller 104 may additionally be comprised of the logic element of a quantum computer. The controller 104 may use logic operations to perform computations and may be in communication with one or more memories 106, such as for storing data, and a communications interface 108, such as for sending and receiving data to and from other controllers 104 or devices. In some cases, the computing device may include one or more processors adapted to execute any operating system. The system and methods described herein may be under the control of one or more processors. The one or more processors many have access to computer-readable storage media ("CRSM"), which may be any available physical media accessible by the processor(s) to execute instructions stored on the CRSM.

In some implementations, a memory 106 is a medium for storing data. The memory 106 may be volatile memory, such as random-access memory (RAM) which is a cache used by the controller 104 for temporary storage of data for use in computations or persistent memory, such as solid-state drive (SSD), hard disk drive (HDD) or other storage devices including tape drives, flash drives, memory cards, optical drives such as compact disk (CD), digital video disk (DVD), or Blu-ray disc, or data storage on nontraditional mediums. In some cases, the memory is a physical, non-transitory, computer-readable medium. The memory may further include Flash memory, read-only memory (ROM), electrically erasable programmable read-only memory (EEPROM), or any other medium which can be used to store the desired information, and which can be accessed by the processor(s).

A communications interface 108, also known as a network interface, is an interface for a device or controller 104 to communicate with another device, controller 104 or network resource such as a cloud 116 server or drive. A communications interface 108 may be wired, such as ethernet cables or universal serial bus (USB) cables, or wireless as in Wi-Fi, Bluetooth, Bluetooth Low Energy (BLE), infrared, near field communications (NFC), 4G long-term evolution (LTE), 5G, or any suitable electromagnetic communication protocol that my involve radio waves, light, etc.

An imaging device 110 is any device capable of detecting sound or electromagnetic waves and assembling a visual representation of the detected waves. An imaging device 110 may collect waves from any part of the electromagnetic spectrum or sounds at any range of frequencies, often as a matrix of independently acquired measurements representing a pixel of a two or three-dimensional image. These measurements may be taken simultaneously or in series via a scanning process or a combination of methods. In addition, some pixels of an image produced by an imaging device may be interpolated from direct measurements representing adjacent pixels to increase the resolution of a generated image.

A wearable device 112 is a digital device capable of being worn or carried. The wearable device 112 may comprise a memory 111, at least one sensor 114 and may further include a controller 113, and a communications interface 115 such as for sending and receiving data to and from another device such as a mobile device 102. A wearable device 112 may be any of a smart watch, fitness tracker, armband, earbuds, ring, gloves, hat, wearable sensor or sensor affixed to or embedded within clothing or applied directly to the skin. In some cases, the sensor 114 is a biometric sensor. As used herein, a biometric sensor is a broad term and refers to any sensor that is capable of obtaining information about a patient, such as a measurement, analysis, characteristic and the like. Sensors that measure blood pressure, temperature, heart rate, respiration, blood oxygen, blood glucose, acceleration, shock, mood, stress, pressure, flow, acoustics, magnetic field, or obtain images are all considered biometric sensors. A mobile device 102 may additionally function as a wearable device 112 when placed in a pocket or carried. A wearable device 112 may communicate data in real-time or may store data locally to be read by a mobile device 102 or other computing device. A wearable device 112 may alternatively comprise a reflective material or a device emitting electromagnetic waves or sounds which may be used by a mobile device 102 or sensor 114 which is not worn by the patient to track the patient's movements. In some cases, a wearable device may comprise a processor and/or memory in a housing that may not be worn by a patient, but may be located near or adjacent a patient. A sensor may be located on the patient and communicate with the wearable device, either through a wired or wireless communication. For example, a wearable device may be located next to a patient, and one or more sensors may be applied to the patient's skin, finger, head, chest, or other body part, and may send sensor data to the wearable device. The wearable device 112 may receive the sensor data and store, analyze, send, generate additional data, and/or generate alerts based upon the sensor data.

A sensor 114 is an input device for measuring a physical quantity and outputting the measurements as a signal which is saved as data representing the measured physical quantity. Sensors 112 may measure a range of physical quantities such as a temperature, distance, movement, acceleration, orientation, size, a change in size, sound frequency, wavelength and intensity, wavelength and intensity of light and other electromagnetic waves, volatile gases, capacitance, resistance, induction, etc. A sensor 114 may output an analog or a digital signal.

A sensor 114 may be embedded in or affixed to a mobile device 102 or a wearable device 112. A sensor 114 may alternatively be discrete from a mobile device 102 or wearable device 112 but be in communication with a device such as a mobile device 102 or a wearable device 112 such as by a communications interface 108, which may be wired or wireless. Alternatively, data may be stored local to the sensor 114 which may be later accessed by a device such as a mobile device 102 or a wearable device 112. A sensor 114 may additionally refer to an array of sensors 112 such as an image sensor 114 for capturing multiple measurement values simultaneous and which may be used to create multidimensional representations of the data such as images.

A cloud 114 is a distributed network of computers comprising servers and databases. A cloud 114 may be a private cloud 114, where access is restricted by isolating the network such as preventing external access, or by using encryption to limit access to only authorized users. Alternatively, a cloud 114 may be a public cloud 114 where access is widely available via the internet. A public cloud 114 may not be secured or may be include limited security features. The cloud 114 may store one or more databases that may be accessible by the mobile device 102 and/or the wearable device 112, and other computing resources. For example, a cloud 114 may include a patient database 118, a qualitative assessment 120, a qualitative assessment module 122, a training module 1245, a monitoring module 126, among others.

The patient database 118 stores data associated with one or more patients. The data may include gender, age, height, weight, previously diagnosed medical conditions, medical history, family medical history, allergies, and vital information such as baseline measurements of heart rate, blood pressure, blood oxygen saturation and respiration rate. The data may be collected from sensors 114 or imaging devices 110 such as those in a wearable device 112 or a mobile device 102 or may alternatively be collected from medical records. In some embodiments, the patient database 118 may comprise patient medical records created by one or more medical professionals.

The qualitative assessment database 120 includes data about one or more qualitative assessments, including the steps or prompts needed to provide to a patient and the method of observing and acquiring patient data, including sensors 114 or imaging devices 110. The qualitative assessment database 120 additionally stores at least one assessment model, artificial intelligence, that uses conversational prompts to instruct a patient to respond with a verbal response or an action.

The qualitative assessment module 122 queries the qualitative assessment database 120 and selects the appropriate assessment model, triggers the training module 124 to train the assessment model, and then triggers the monitoring module 126 to provide prompts to the patient and monitor the patient's responses to provided prompts. A quantitative score is returned to the qualitative assessment module, which is used to determine a clinical qualitative assessment result According to some embodiments, the training module 124 queries the patient database 118 for patient data from previous patient visits and trains an assessment virtual assistant artificial intelligence to collect sensor 114 data and/or data from imaging devices 110 and converses with a patient or patient caregiver and selects the most likely diagnosis based on the information received from the sensors 112 and patient responses.

The monitoring module 126 uses data from the patient database 118 and the qualitative assessment database 120 to provide prompts to a patient and then may use sensors 114 and/or imaging devices 110 to monitor the patient responses. The patient responses may be verbal or may comprise one or more actions to be performed by the patient and observed by one or more sensors 114 or imaging devices 110. The monitoring module 126 further assigning a quantitative score to each patient response and providing additional prompts if indicated by the qualitative assessment database 120. The monitoring module 126 then determines a final score which is then provided to the qualitative assessment module 122.

Functioning of the "Patient Database" will now be explained with reference to FIG. 2.

FIG. 2 illustrates the patient database 118. The patient database 118 is a database for storing information about one or more patients. The data may include gender, age, height, weight, previously diagnosed medical conditions, medical history, family medical history, medications, allergies, and vital information such as baseline measurements of heart rate, blood pressure, blood oxygen saturation and respiration rate. In some embodiments, the patient database 118 may store at least a portion of a patients Electronic Health Record (EHR). The data may be populated by medical professionals during medical visits such as surgeons, physicians, nurses, emergency medical technicians, etc. In some embodiments, the patient database 118 may be populated by the patient themselves by responding to an intake form. In some cases, the patient database 118 may be populated by the patient themselves, such as by responding to an intake form. The patient database 118 may additionally be populated and updated with patient data from wearable devices 110 such as a smart watch by the monitoring module 126 or the qualitative assessment module 122. The patient database 118 may be used by the training module 124, monitoring module 126, and/or the qualitative assessment module 122, such as to provide historical and baseline patient data. Functioning of the "Qualitative Assessment Database" will now be explained with reference to FIG. 3.

FIG. 3 illustrates the qualitative assessment database 120. Stores qualitative assessments to return quantitative data from subjective data. Such tests include pain scales such as Numerical Rating Pain Scale, Wong-Baker Faces Pain Scale, FLACC Scale, CRIES Scale, COMFORT Scale, McGill Pain Scale, Color Analog Scale, Mankoski Pain Scale, Brief Pain Inventory, Descriptor Differential Scale of Pain Intensity, etc. These tests may also include assessments for conditions being experienced by a patient, including both the onset of a condition and the results from a condition such as commonly used stroke assessment scales including the Cincinnati Prehospital Stroke Scale, Los Angeles Prehospital Stroke Scale, Rapid Arterial Occlusion Evaluation Scale, Glasgow Coma Scale, NIH Stroke Scale, Modified NIHSS scale, Intracerebral Hemorrhage Scale, Berg Balance Scale, Modified Rankin Scale, Barthel Index, Glasgow Outcome Scale, etc. Such assessments are also common in physical therapy to assess a patient's physical abilities and limitations and monitor progress. The assessments may be simple, requiring answering a single question or performing a single action, or may require multiple steps or instructions and observations made using sensors 114 or observations, such as via one or more imaging devices 110 to compare a patient's movements with images acquired during previous assessments using a trained assessment artificial intelligence capable of classifying the patient's movements or other response and assigning a quantitative score. Traditionally these qualitative assessments are administered by a trained professional who assigns subjective scores based on their observations. The qualitative assessment database 120 is populated by trained medical professionals, including doctors, nurses, physical therapists, and researchers who may develop new qualitative assessments. The assessment artificial intelligence may also be updated by the training module 124 and used by the qualitative assessment module 122, training module 124, and the monitoring module 126. The qualitative assessment database 120 may be located on a cloud 116 or a local memory 106. The qualitative assessment database 120 may alternatively be a third-party database or a collection or third-party databases.

Functioning of the "Qualitative Assessment Module" will now be explained with reference to FIG. 4.

Figure 4:
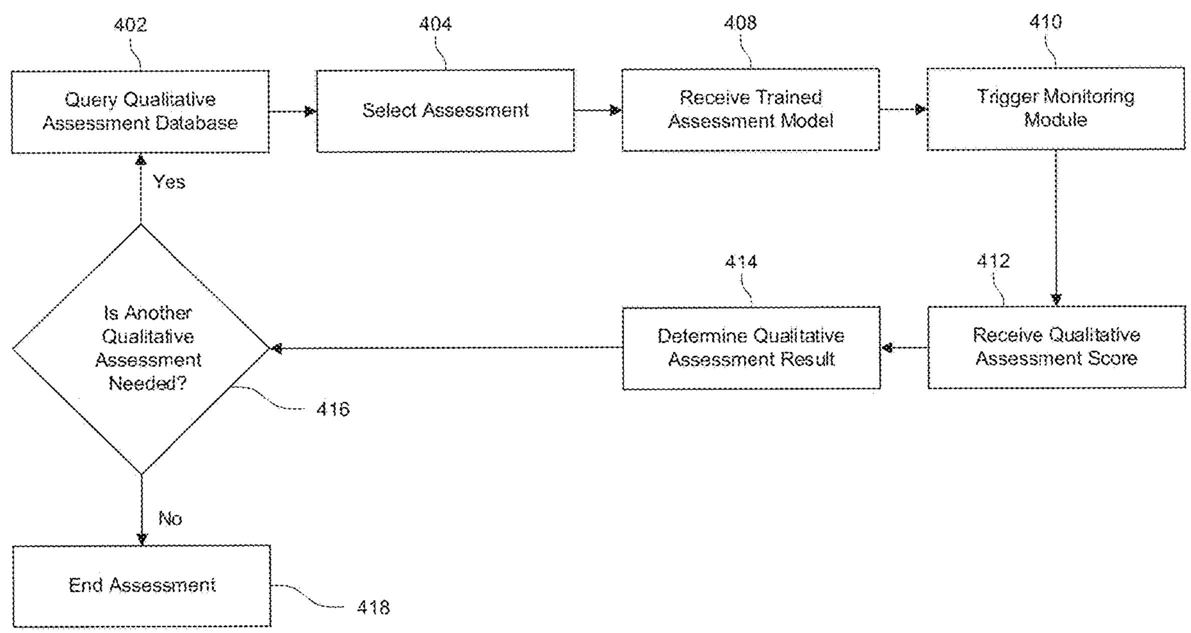
FIG. 4 illustrates a qualitative assessment module, in accordance with some embodiments.

FIG. 4 illustrates the qualitative assessment module 122. The process begins with querying, in step 402, the qualitative assessment database 120 for a qualitative assessment. A qualitative assessment may comprise a series of questions or prompts that a patient responds to verbally or by performing a requested action that may be observed and used to provide a quantitative score representing a qualitative observation. Such assessments are typically subjective, relying upon a patient's prior experiences, tolerances, or the experience of a trained professional administering the assessment. As an example, the qualitative assessment module 122 may request that a patient raise their arm to demonstrate a range of motion, and the range of motion may be captured by one or more imaging sensors, and the imaging data captured by the one or more imaging sensors may be analyzed to determine the range of motion, which may be quantified. For instance, where a range of motion is less than an expected range of motion, a score, such as a percentage, may be associated with the patient's range of motion. The process may include selecting, in step 404, a qualitative assessment to be performed. The qualitative assessment may require a verbal response or may require the patient to act in response to a verbal prompt. The assessment may utilize objective measurements and may include subjective observations made by the patient or a trained professional. In some embodiments, selecting an assessment may include using the Berg balance scale.

The process may include triggering, in step 406, the training module 124 to train or update an assessment model. The training module 124 may retrieve data from the patient database 118 and/or the qualitative assessment database 120 and may use the data to predict the patient's quantitative result or score. The training module 124 may use the actual quantitative result or score resulting from the traditional administration of the qualitative assessment to determine whether the prediction was correct and updating the assessment model. The updated assessment model may then be saved to the qualitative assessment database 120. According to some embodiments, the process includes providing an assessment module using the Berg balance scale.

The process may include receiving, in step 408, the trained or updated assessment model from the training module 124 as saved in the qualitative assessment database 120. The updated assessment model may include at least an artificial intelligence machine learning model trained on patient data from patients assessed using the selected qualitative assessment. For example, one or more machine learning algorithms may be used and trained on patient data and used to generate more accurate patient assessments. The one or more machine learning algorithms may use any one or combination of algorithms, which may include neural networks, linear regression, nearest neighbor, Bayesian, clustering (e.g., k-means clustering), natural language procession, sentiment detection, or other algorithms either alone or in combination. Additional algorithms that may be used singularly or in combination with one or more other algorithms include logistic regression, decision trees, random forest, and dimensionality reduction operations. These various sets of algorithms may be developed and/or trained by using data coming from a single source (e.g., patient data records), or by combining and merging data from different sources, or by coming in data sources and utilizing one or more of prediction, outcomes, or results coming from the algorithms developed at the early stages.

In some embodiments, the process includes receiving a trained assessment model for administering and interpreting patient responses using a Berg balance scale. The process may include triggering, in step 410, the monitoring module 126 to collect patient data from sensors 114 and/or imaging devices 110, which may be located on the patient via a wearable device 112, mobile device 102, or from other sensors 114 or imaging devices 110 which may be affixed to or oriented towards the patient. The monitoring module 126 may further query the patient database 118 and compare the patient data collected from the sensors 114 and imaging devices 110 to historical and baseline data stored in the patient database 118, such as to determine whether the measured values are within a normal range for the patient. For instance, a range of motion of the patient's rotator cuff can be captured through imaging sensors and compared with historical baseline data to determine whether there has been a change in the patient's range of motion. In some cases, the monitoring module 126 is provided with a trained assessment model for administering and interpreting patient responses using a Berg balance scale.

The process may include receiving, in step 412, a final qualitative assessment score from the monitoring module 126. The qualitative assessment score may include at least one quantitative result representing a qualitative assessment result. The qualitative assessment score may alternatively be a set of quantitative results, each representing a subset of quantitative scores from independent steps or prompts to the patient. In some cases, the process may receive a Berg balance scale score of 44, and determine, in step 414, a clinical qualitative assessment result based upon the qualitative assessment score received from the monitoring module 126. The clinical qualitative assessment may be determined by comparing the quantitative score received from the monitoring module 126 and comparing it to data stored in the qualitative assessment database 120. The data may comprise a reference table such that the quantitative score represents a corresponding clinical qualitative assessment or diagnosis. In an example, the patient's Berg balance scale score of 44 is less than a threshold of 45, indicating that the patient is at an increased risk of falling. The Berg balance scale score may then be used by other modules of the system to store, analyze, and assess the patient risks and for predicting a diagnosis, or further care.

The process may include determining, in step 416, whether an additional qualitative assessment is needed. An additional qualitative assessment may be needed if indicated by data stored in the qualitative assessment database 120 based on the result from the previous qualitative assessment and/or if selected by a medical professional. For example, if a first qualitative assessment does not indicate the presence of the condition for which the patient was being assessed though symptoms remain present, a second qualitative assessment may be performed to identify the patient's present condition. In some embodiments embodiment, no additional qualitative assessment is needed.

The process may conclude, at step 418, the qualitative assessment as no additional qualitative assessment may be necessary.

Figure 5:
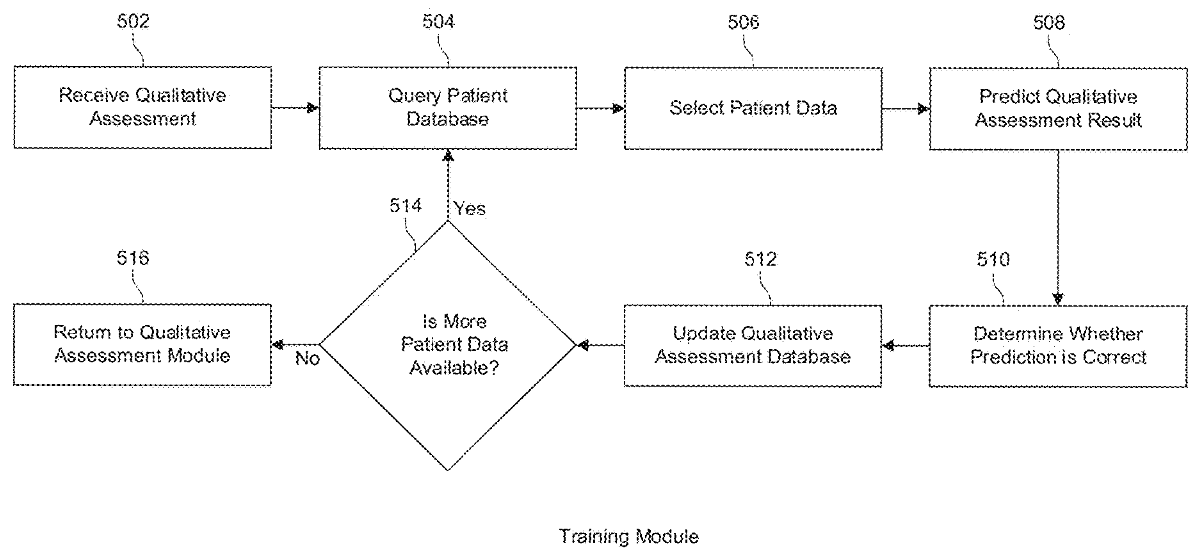
FIG. 5 illustrates a training module, in accordance with some embodiments.

FIG. 5 illustrates functioning of the "Training Module," according to some embodiments.

FIG. 5 illustrates the training module 124. The training module 124 may store, execute, retrieve, or otherwise take advantage of a machine learning model to assess a patient. In some embodiments, one or more machine learning algorithms may be applied. For example, a set of one or more algorithms may be stored in memory or on a storage device and, when executed by one or more processors, cause the processors to perform acts according to the one or more algorithms. Machine learning is a type of artificial intelligence that allows computer systems to gradually become more efficient and proficient at a specific task. In many cases, machine learning is facilitated by large amounts of data that the computer systems can apply statistical operations to make accurate predictions based on new inputs. One or more algorithms stored in the memory allow collection of large amounts of data over time, and through an iterative process, generate more and more accurate predictions. In some cases, training data, or sample data, is provided to the computer systems to train the system as to which outputs are consistent with the inputs. The machine learning algorithms may be stored on the mobile device 102, or on the cloud 116, or may be stored in some other location, such as, without limitation, on a remote computing device, a distributed computing environment, or some other location or device. In some cases, the mobile device may store and execute the machine learning algorithms, while in other cases, the assessment virtual assistant accesses the machine learning algorithms that are stored and executed on remote computing resources. The remote computing resources may comprise a distributed computing architecture, such as cloud computing 116, or may comprise one or more server computers that may be accessed remotely, such as over a network, such as the internet.

The set of algorithms may include any suitable algorithms, and may include one or more of neural networks, linear regression, nearest neighbor, Bayesian, clustering, (e.g., k-means clustering), natural language processing, sentiment detection, or other algorithms either alone or in combination. Some additional algorithms that may be used singularly or in combination with one or more other algorithms include logistic regression, decision trees, random forest, and dimensionality reduction operations. These various set of algorithms may be developed by using data coming from a single source (patient data records); or by combining and merging data from different sources outlined; or by combining data sources and utilizing one or more of prediction, outcomes, or results coming from the algorithms developed at the early stages.

The process begins with receiving, in step 502, a qualitative assessment from the qualitative assessment module 122. The qualitative assessment may comprise a series of steps or prompts to be provided to the patient as instructions requiring a verbal response or the performance of one or more physical movements or actions. The patient responses may be observed, analyzed, and used to determine a quantitative score to determine a qualitative assessment of one or more aspects of the patient's physiology or mental capabilities. In an example, the selected qualitative assessment may rely on the Berg balance scale.

The process may include querying, in step 504, the patient database 118 for patient data from previously administered assessments. The patient data may include data from various qualitative assessments with a shared purpose; such as, for example, there are multiple assessments for measuring pain, including the Numerical Rating Pain Scale, Wong-Baker Faces Pain Scale, FLACC Scale, CRIES Scale, etc. In an example, the process retrieves patient data relating to assessing a patient's fall risk, which may be used to determine a present or future fall risk.

The process may include, in step 506, patient data representing a single patient who was previously assessed with a qualitative assessment. The data may include the patient responses to each prompt or instruction provided to the patient and the quantitative scores and final assessment results for the patient's assessment. In an example, the patient data representing data for a patient who was assessed for fall risk, the data including the detailed results of an assessment using the Berg balance scale.

The process may include predicting, in step 508, that the results are assigned to the observed patient data based on the provided observed patient data. The patient data may be measured and/or observed vital signs and/or text-based observations made by a trained medical professional administering the assessment. Alternatively, the patient data may be a series of images or videos taken using an imaging device 110, or a combination of patient data input methods. Similarly, the patient data may be acquired by one or more sensors 114, which may be located on a wearable device 112 worn by the patient. In an example, the patient data is image data acquired by an imaging device 110, and the predicted value is a 4.

The process may include determining, in step 510, whether the prediction is correct by comparing the predicted value to the value stored in the patient database 118. The prediction is correct if the prediction matches the value stored in the patient database 118 and is incorrect if the prediction does not match the stored value. The data in the patient database may be considered ground truth data, or actual prior measured values. In some examples, the predictions are measured against ground truth data to ascertain accuracy of the prediction model and to further train and refine the model. In an embodiment, the predicted value of 4 does not match the value of 3 stored in the patient database 118. The stored value may have been determined by another assessment module or may have been determined by a trained medical professional who administered the assessment and determined the value based on their assessment. The model may be iterated by making predictions, comparing the predictions with ground truth data, and updating the model so that the predictions begin to more closely match the ground truth data.

The process may include updating, in step 512, the qualitative assessment database 120 and the assessment module using the result of the prediction. If the prediction was correct, reinforcing the machine learning model forming the assessment model's artificial intelligence. If the prediction was incorrect, using a regression model or other form of algorithmic or machine learning, such as those described elsewhere herein, to adjust the assessment model.

The process may include determining, in step 514, whether additional patient data is available to train the assessment model. In an embodiment, there is additional fall risk data in the patient database 118 and therefore querying the patient database 118 for the additional patient data. There is no additional patient data assessing fall risk in the patient database in an alternate embodiment, returning, in step 516, to the qualitative assessment module 122 with the trained assessment module. In an embodiment, returning the trained assessment module using the Berg balance scale.

In some cases, the Training module 124 may be trained with sample data, such as from a database containing patient data and a prior diagnosis from a medical care provider. The patient data may be input into the model and the prediction may be compared against the prior diagnosis from a medical care provider. If the prediction matches the diagnosis, then the prediction is correct. If, however, the prediction does not match the diagnosis, the model may be trained to associate the patient data with a particular diagnosis and the model is updated and trained. In this way, the machine learning system can compare its predicted data against real-world data and modify the one or more machine learning algorithms based upon this comparison. In some cases, the processes described herein may be carried out automatically and may be performed without human intervention in some cases. This allows for a large volume of data points to be captured, aggregated, processed, and stored. In some cases, the volume of data points exceeds thousands, tens of thousands, hundreds of thousands, or millions, or greater. The Training module 124 may analyze the aggregated data points and through iterative training on the machine learning algorithms, continuously improve its prediction accuracy.

Functioning of the "Monitoring Module" will now be explained with reference to FIG. 6.

Figure 6:
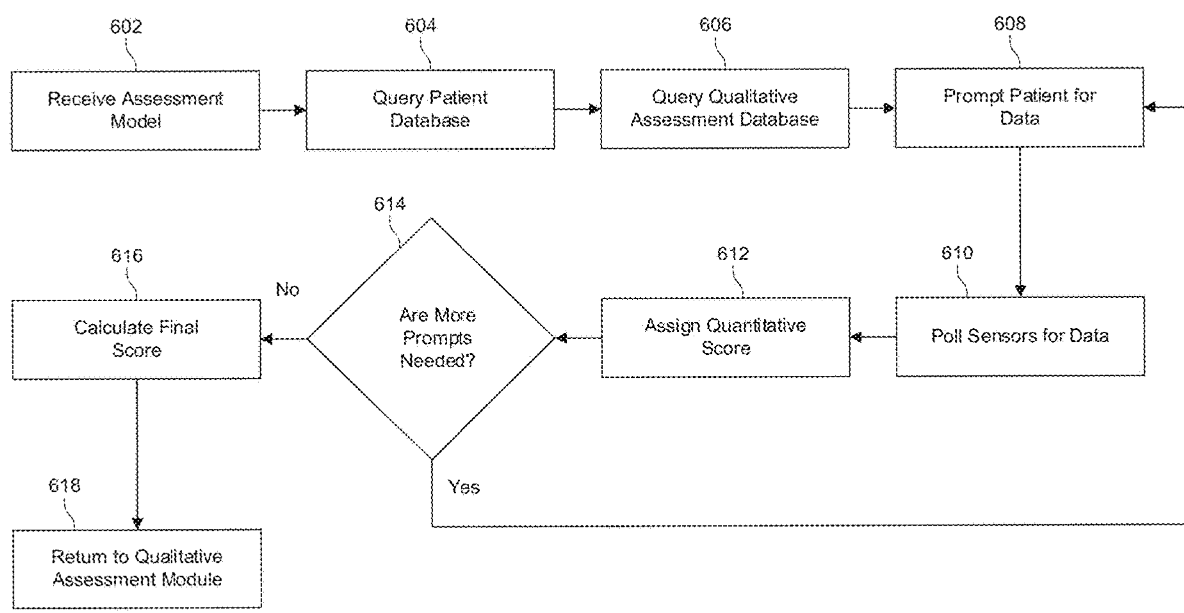
FIG. 6 illustrates a monitoring module, in accordance with some embodiments.

FIG. 6 illustrates the monitoring module 126. The process begins with receiving, in step 602, an assessment model from the qualitative assessment module 122. The assessment model may be an artificial intelligence using machine learning to accurately assess a patient's responses or predict a score that a trained medical professional would otherwise assign. In some embodiments, the assessment model is an algorithmic program utilizing protocols or procedures to assess a patient's responses and accurately predict a score that a trained medical professional would otherwise assign. In an embodiment, the assessment model may be trained to assess a patient's fall risk using the Berg balance scale. The monitoring module 126 may access imaging data and apply one or more algorithms to interpret motion which may be compared against a kinematic human model to determine a score based upon motion of the patient.

The process of the monitoring module may include querying, in step 604, the patient database 118 for historical patient data. The previous patient data may be specific for the patient for which a sensor 112 or imaging device 110 measurements may be taken. If specific patient data is not available, data may be retrieved for a group of patients, such as all patients matching select parameters such as gender, age, and prior medical history. Similarly, a predefined generic baseline value may be retrieved from the patient database 118. In an example, the patient's average pulse is 60-100 beats per minute, and normal blood oxygen concentration is above 95, which may be determined to be baseline numbers. Alternatively, the patient's previous Berg balance scale score may be 50, which may be relied on as a baseline threshold value.

The process may include querying, in step 606, the qualitative assessment database 120 for the next step in a qualitative assessment procedure. The next step in the qualitative assessment procedure may include an instruction to be given to a patient requiring a verbal or physical response. The next step may additionally or alternatively comprise sensor 114 data, such as a motion-tracking device or an imaging device. In an example, the next step may be a Berg balance scale evaluation by prompting the patient to move from a seated position to a standing position, which may be monitored by a sensor 114 which may include one or more accelerometers in a wearable device 112, an image sensor, or some other sensor or combination of sensors.

The process may include prompting, in step 608, the patient for data by asking a question in a conversational manner. The question may be presented via a visual interface, or in some embodiments, is announced verbally via a virtual assistant. In an example, the virtual assistant may ask the patient to "please sit down," and upon confirming that the patient is seated, further asking the patient to "stand up without using your hands." The patient may ask questions that the assessment module may comprehend using natural language processing, and a response to the patient may be generated. For example, if the patient were to ask, "does it matter which chair I sit in?" The assessment module may generate the response, "No, any chair of normal height may be used."

The process may include polling, in step 610, at least one sensor 114 or imaging device 110 monitoring the patient. The sensor 114 or imaging device 110 may be located on the patient, such as being worn as a wearable device 112, carried as in a mobile device 102, or alternatively may be positioned away from the patient but in a position to be able to monitor the patient. In an example, the sensor 114 is a microphone for receiving a verbal reply from the patient. In an alternate example, the sensor 114 is an imaging device 110 for capturing the patient's physical movements made in response to a prompt, such as to monitor the action of a patient moving from a seated position to a standing position. Alternatively, an accelerometer or other sensors may monitor the patient's position while moving from a seated to a standing position. Any type of sensor or combination of sensors may be employed to interact with, and monitor, the patient and the patient's movements.

The process may include assigning, in step 612, a quantitative score to the patient's response to the prompt provided to the patient. The patient's response may be verbal or may comprise a physical action. In an example, the prompt may instruct the patient to "walk in a straight line," and the patient's response is to walk in a straight line until another prompt is given to the patient to "stop." If a verbal response is given, the system may use natural language processing to determine a numerical score associated with the patient's response. In an example, in response to the prompt, "what is your current severity of pain on a scale of 0 to 10 where 0 is no pain and 10 is the worst pain you have ever felt?" the patient replying "6" and using natural language processing to determine that the patient provided a value of 6 and assigning 6 to the quantitative score of the patient's pain. If the patient's response is physical, sensors 114 such as accelerometers on a wearable device 112 worn by the patient may be used to track a patient's movement. Alternatively, one or more imaging devices 110 may be used to capture images of the patient, and image processing and recognition can be used to determine a variation from a baseline value. In an assessment using the Berg balance scale, the patient, having been prompted to move from a seated position to a standing position without using their hands, having done so without difficulty or loss of balance, is assigned a quantitative score of 4.

The process may include determining, in step 614, whether additional prompts are needed. Additional prompts may be needed if additional steps are required to complete the qualitative assessment. Similarly, additional prompts may be necessary if the patient's response was insufficient to assign a quantitative score. In such cases, an additional prompt clarifying or correcting the patient's action may be required, such as if a patient were instructed to "walk 30 meters" and only walked 10 meters. Alternatively, the patient may ask a question to clarify what is being requested to them. In an example, another step may be needed to complete the quantitative assessment; the next step may include prompting the patient to "continue standing still for two minutes without touching anything."

The process may further include the step of determining, in step 616, a final score for the qualitative assessment. The final score may be cumulative, where the quantitative scores assigned to each step in the qualitative assessment may be summed. Alternatively, the final score may be an average of the quantitative scores assigned to the patient's responses. The final score may be further a weighted score, such that the quantitative score assigned to one patient response may be provided a weight by multiplying the score by a predetermined value that is different from a second quantitative score assigned to a second patient response. In an example, the process includes summing the scores provided for each step of the Berg balance scale and determining the patient's final score to be 44.

The process may include returning, in step 616, to the qualitative assessment module 122, with the final score. Multiple final scores may be provided in some embodiments, where each score may represent a part of the qualitative assessment. For example, upon completion of one or more assessment tasks, the process may return a Berg balance scale score of 44 to the qualitative assessment module 122, which may use the score for analysis, for treatment recommendations, for medication recommendations, or as diagnostic information for a medical professional.

Figure 7:
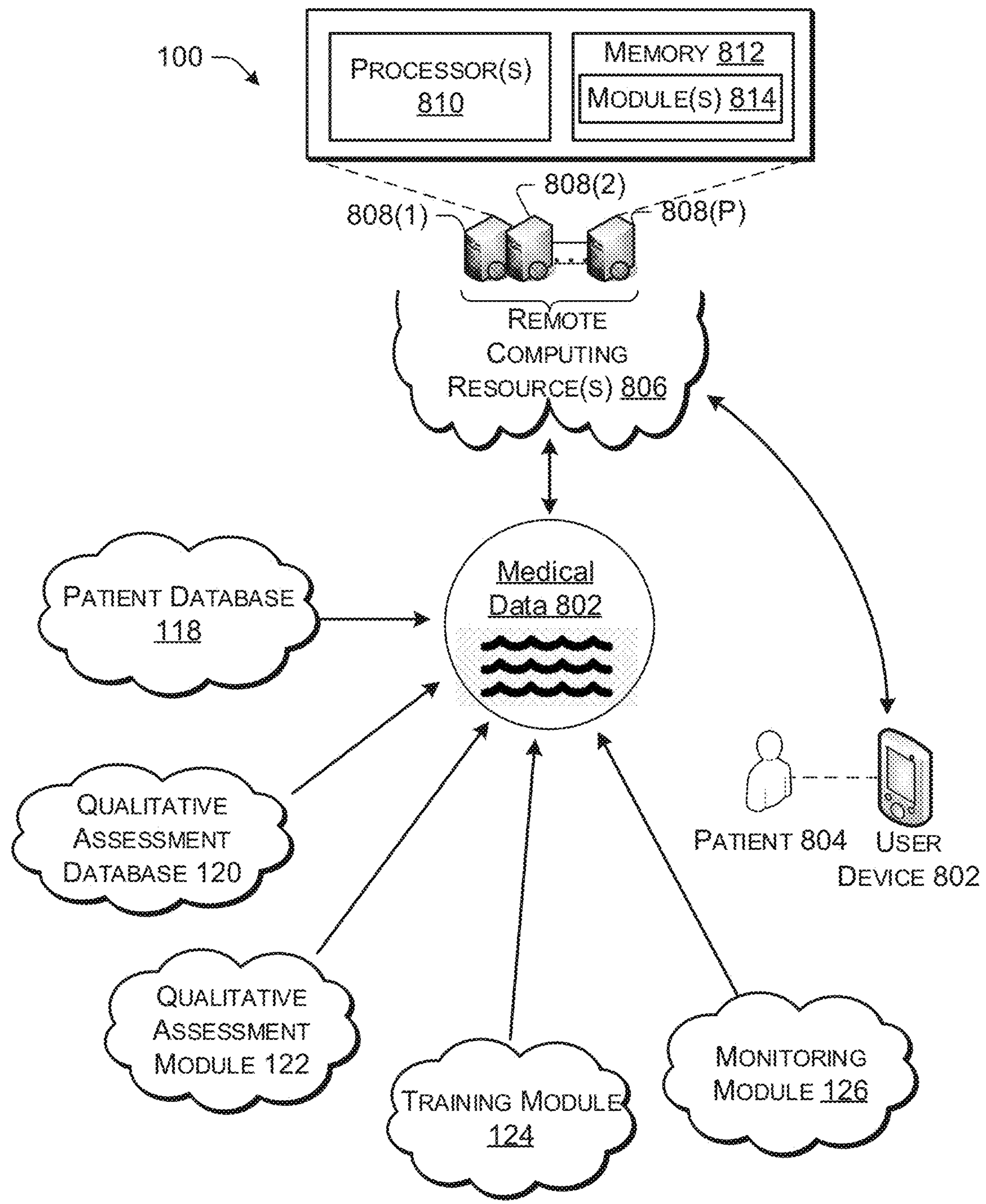
FIG. 7 illustrates an assessment virtual assistant, in accordance with some embodiments.

With reference to FIG. 7, an assessment virtual assistant system 100 is illustrated. In a non-limiting example, the assessment virtual assistant 100 may include instructions that are executed on a computing device 802 associated with a patient 804. For instance, the assessment virtual assistant 100 may be executed by a smart phone, laptop computer, tablet computer, gaming system, set-top box, hand-held computing device, smart watch, or some other device that is associated with the patient. In some cases, the assessment virtual assistant 100 may be executed on a kiosk at a medical care facility. For example, a kiosk may be provided for a patient upon entry to a medical care center, such as a hospital or clinic, and the patient interacts with the kiosk during a check-in procedure, which may provide an initial assessment of the patient.

The assessment virtual assistant 100 may function as substantially described herein. In some cases, the assessment virtual assistant 100 may interact with remote computing resources 806, which may comprise one or more server computers 808(1), 808(2), 808(P), or a distributed server farm, or cloud storage, or some other computing architecture. The remote computing resources 806 may have one or more processors 810 and memory 812. The memory 812 may store one or more modules 814 that are executed by the processors 810 to carry out many of the instructions, routines, tasks, and operations described herein. In some embodiments, the processor(s) 810 include a central processing unit (CPU), a graphics processing unit (GPU), both CPU and GPU, or other processing units or components known in the art. Additionally, each of the processor(s) 810 may possess its own local memory, which also may store program modules, program data, and/or one or more operating systems. The processor(s) 810 may include multiple processors 810 and/or a single processor 810 having multiple cores.

In some instances, the remote computing resources 806 may be a computing infrastructure of processors 810, storage (e.g., memory 812), software (e.g., modules 814), data access and so forth that is maintained and accessible via a network, such as the internet. The remote computing resources 806 may not require end-user knowledge of the physical location and configuration of the system that delivers the services. Common expressions associated with these remote computing resources 806 may include "on-demand computing", "software as a service (SaaS)", "platform computing", "network-accessible platform", "cloud services", "data centers", and so forth.

Those skilled in the art will appreciate that embodiments described herein can be practiced on or in conjunction with other computer system configurations beyond those described herein, including multiprocessor systems, microprocessor-based or programmable consumer electronics, minicomputers, mainframe computers, handheld computers, personal digital assistants, e-readers, mobile telephone devices, tablet computing devices, special-purposed hardware devices, network appliances, and the like. The configurations described herein can also be practiced in distributed computing environments, such as a distributed computing network, where tasks can be performed by remote computing devices that are linked through a communications network. In a distributed computing environment, program modules can be located in both local and remote memory storage devices.

The memory 812 may include computer readable storage media (CRSM), which may be any available physical media accessible by the processor(s) 810 to execute instructions stored on the memory 812. In one basic implementation, CRSM may include random access memory (RAM) and Flash memory. In other implementations, CRSM may include, but is not limited to, read-only memory (ROM), erasable programmable ROM (EPROM), electrically erasable programmable read-only memory (EEPROM), or any other medium which can be used to store the desired information, and which can be accessed by the processor(s) 810. As will be discussed in additional detail, the memory 812 may include an operating system, and one or more modules 814. The memory 812 may be a physical memory device, which physically embodies the modules and instructions, and is non-transitory computer readable memory.

As described herein, the assessment virtual assistant 100 may be configured to determine an assessment of a patient, such as by interacting with the patient or prompting the patient for information or to complete tasks. The results of the interaction may be converted to scores and compared with baseline values to further determine a patient assessment. In some cases, the assessment virtual assistant can act autonomously by receiving sensor data, obtaining additional data based on the sensor data, generate communications to elicit further information from the patient, which may include natural language processing, image analysis, and may be configured to automatically generate an assessment, make recommendations, or alert a medical professional, and others.

It should be appreciated that the subject matter presented herein can be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations can be performed in combination with other types of program modules. Generally, program modules include routines, programs, components, data structures, and other types of structures that perform particular tasks or implement particular abstract data types.

The remote computing resources 806 may be communicatively coupled to the medical data 802 (e.g., patient database) via wired technologies (e.g., CAT5, USB, fiber optic cable, etc.), wireless technologies (e.g., RF, cellular, satellite, Bluetooth, etc.), or other suitable connection technologies. In some cases, the medical data 802 is stored on the memory 812 of the remote computing resources 806.

A user device 802 associated with a patient 804 may be able to access the remote computing resources 806, the medical data 802, and/or one or more of the modules 814 stored on the memory 812. The user device 802 may receive one or more outputs of the one or more modules 814 as described herein.

The medical data 802 may store, or have access to, additional data sources. For instance, the medical data 802 may include one or more of a patient database 118, a qualitative assessment database 120, a qualitative assessment module 122, a training module 124, a monitoring module 126, among other sources of information.

In some cases, the patient database and 119/or the qualitative assessment database 120 may be accessible through a wireless network, such as the internet, and may be stored in a distributed computing environment, such as a cloud computing architecture. Similarly, the qualitative assessment module 122, training module 124, and/or monitoring module 126 may be stored remotely from the computing device associated with the patient. Nevertheless, the computing device 802 may have credentials that allow it to access the patient database, qualitative assessment module 122, training module 124, and/or monitoring module 126 to interact with the patient and determine a patient assessment. In some cases, the computing device associated with the patient may receive biometric data associated with the patient from one or more sensors in contact with, or pointed at, the patient, as described elsewhere herein.

The disclosure sets forth example embodiments and, as such, is not intended to limit the scope of embodiments of the disclosure and the appended claims in any way. Embodiments have been described above with the aid of functional building blocks illustrating the implementation of specified functions and relationships thereof. The boundaries of these functional building blocks have been arbitrarily defined herein for the convenience of the description. Alternate boundaries can be defined to the extent that the specified functions and relationships thereof are appropriately performed.

The foregoing description of specific embodiments will so fully reveal the general nature of embodiments of the disclosure that others can, by applying knowledge of those of ordinary skill in the art, readily modify and/or adapt for various applications such specific embodiments, without undue experimentation, without departing from the general concept of embodiments of the disclosure. Therefore, such adaptation and modifications are intended to be within the meaning and range of equivalents of the disclosed embodiments, based on the teaching and guidance presented herein. The phraseology or terminology herein is for the purpose of description and not of limitation, such that the terminology or phraseology of the specification is to be interpreted by persons of ordinary skill in the relevant art in light of the teachings and guidance presented herein.

The breadth and scope of embodiments of the disclosure should not be limited by any of the above-described example embodiments but should be defined only in accordance with the following claims and their equivalents.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

Unless otherwise noted, the terms "connected to" and "coupled to" (and their derivatives), as used in the specification, are to be construed as permitting both direct and indirect (i.e., via other elements or components) connection. In addition, the terms "a" or "an," as used in the specification, are to be construed as meaning "at least one of" Finally, for ease of use, the terms "including" and "having" (and their derivatives), as used in the The specification and annexed drawings disclose examples of systems, apparatus, devices, and techniques that may provide medical patient interaction and assessment. It is, of course, not possible to describe every conceivable combination of elements and/or methods for purposes of describing the various features of the disclosure, but those of ordinary skill in the art recognize that many further combinations and permutations of the disclosed features are possible. Accordingly, various modifications may be made to the disclosure without departing from the scope or spirit thereof. Further, other embodiments of the disclosure may be apparent from consideration of the specification and annexed drawings, and practice of disclosed embodiments as presented herein. Examples put forward in the specification and annexed drawings should be considered, in all respects, as illustrative and not restrictive. Although specific terms are employed herein, they are used in a generic and descriptive sense only, and not used for purposes of limitation.

Those skilled in the art will appreciate that, in some implementations, the functionality provided by the processes and systems discussed above may be provided in alternative ways, such as being split among more software programs or routines or consolidated into fewer programs or routines. Similarly, in some implementations, illustrated processes and systems may provide more or less functionality than is described, such as when other illustrated processes instead lack or include such functionality respectively, or when the amount of functionality that is provided is altered. In addition, while various operations may be illustrated as being performed in a particular manner (e.g., in serial or in parallel) and/or in a particular order, those skilled in the art will appreciate that in other implementations the operations may be performed in other orders and in other manners. Those skilled in the art will also appreciate that the data structures discussed above may be structured in different manners, such as by having a single data structure split into multiple data structures or by having multiple data structures consolidated into a single data structure. Similarly, in some implementations, illustrated data structures may store more or less information than is described, such as when other illustrated data structures instead lack or include such information respectively, or when the amount or types of information that is stored is altered. The various methods and systems as illustrated in the figures and described herein represent example implementations. The methods and systems may be implemented in software, hardware, or a combination thereof in other implementations. Similarly, the order of any method may be changed, and various elements may be added, reordered, combined, omitted, modified, etc., in other implementations.

The processor as disclosed herein can be configured with instructions to perform any one or more steps of any method as disclosed herein.

From the foregoing, it will be appreciated that, although specific implementations have been described herein for purposes of illustration, various modifications may be made without deviating from the spirit and scope of the appended claims and the elements recited therein. In addition, while certain aspects are presented below in certain claim forms, the inventors contemplate the various aspects in any available claim form. For example, while only some aspects may currently be recited as being embodied in a particular configuration, other aspects may likewise be so embodied. Various modifications and changes may be made as would be obvious to a person skilled in the art having the benefit of this disclosure. It is intended to embrace all such modifications and changes and, accordingly, the above description is to be regarded in an illustrative rather than a restrictive sense.

What is claimed is:

1. A method under control of one or more computing devices, the method comprising:

receiving, from a patient database, patient data associated with a patient;

receiving, from a qualitative assessment database, a score associated with a previous qualitative assessment;

selecting a qualitative assessment to be performed;

prompting, based at least in part on the qualitative assessment, the patient to perform a physical action;

predicting, based at least in part on the patient data and the qualitative assessment to be performed, a predicted quantitative result;

generating, from one or more sensors, motion data associated with the physical action of the patient;

determining, based at least in part on the motion data and the previous qualitative assessment, a qualitative assessment, the qualitative assessment including a qualitative assessment score; and generating, based at least in part on the qualitative assessment score, a diagnosis for the patient.

2. The method as in claim 1, wherein the qualitative assessment module comprises a machine learning model and further comprising training the machine learning model on medical training data and medical ground truth data.

3. The method as in claim 1, further comprising generating, by the one or more computing devices, an audible question to the patient and receiving an audible answer from the patient.

4. The method as in claim 3, wherein generating an audible question comprises a text to speech converter that generates the audible question.

5. The method as in claim 3, further comprising performing natural language processing on the audible answer and determining, based at least in part on the audible answer, the qualitative assessment.

6. The method as in claim 1, wherein generating motion data is performed by one or more wearable sensors on the patient.

7. The method as in claim 6, wherein the one or more wearable sensors comprise one or more of a watch, a smart phone, a glove, or a hat.

8. The method as in claim 1, wherein generating the motion data is performed by one or more of a wearable sensor worn by the patient or an imaging sensor aimed at the patient.

9. The method as in claim 1, further comprising determining the physical action of the patient by comparing the motion data against a kinematic model.

10. The method as in claim 1, further comprising comparing the motion data associated with the patient with historical motion data from the patient database and determining that the motion data associated with the patient is within a normal range for the patient.

11. The method as in claim 1, wherein generating the diagnosis for the patient includes a probability that the medical condition is present.

12. The method as in claim 11, further comprising determining that an additional qualitative assessment is needed and performing an additional qualitative assessment of the patient.

13. A system for assessing a medical patient, comprising:

a sensor configured to obtain sensor data associated with physical information about a patient;

a processor configured to process the sensor data to determine a quantitative assessment score;

an assessment engine configured to determine a qualitative assessment based at least in part on the quantitative assessment score and further configured to generate, based at least in part on the qualitative assessment, a diagnosis for the patient;

a machine learning engine configured to predict one or more of the quantitative assessment score, the qualitative assessment, and the diagnosis; and a training module configured to iterate the machine learning engine on the diagnosis with a source of ground truth data to improve the machine learning engine.

14. The system as in claim 13, wherein the machine learning engine is trained on patient data and configured to determine the qualitative assessment.

15. The system as in claim 13, wherein the sensor comprises a microphone and further comprising a natural language processing engine configured to convert an audible patient response to text.

16. The system as in claim 13, wherein the sensor comprises a motion sensor affixed to the patient and configured to obtain motion data of the patient.

17. The system as in claim 13, wherein the sensor is an imaging sensor configured to obtain imaging data of the patient and further comprising an image analysis engine configured to analyze the imaging data to determine whether the imaging data is within a normal range for the patient.

18. The system as in claim 13, wherein the assessment engine is configured to determine the qualitative assessment based at least in part on one or more of motion data, audible responses, and imaging data of the patient.

19. The system as in claim 13, wherein the assessment engine is configured to determine whether a second quantitative assessment score is needed and obtain second sensor data to determine the second quantitative assessment score.

20. The system as in claim 13, wherein the assessment engine is configured to determine a confidence score for the qualitative assessment.

* * * * *